United States Patent [19]

Brydon

[11] Patent Number: 5,740,795
[45] Date of Patent: Apr. 21, 1998

[54] ESTIMATION OF FLOW AND DETECTION OF BREATHING IN CPAP TREATMENT

[75] Inventor: John William Ernest Brydon, Wollstonecraft, Australia

[73] Assignee: ResMed Limited, an Australian Company, North Ryde, Australia

[21] Appl. No.: 348,580

[22] Filed: Dec. 2, 1994

[30] Foreign Application Priority Data

Dec. 3, 1993 [AU] Australia ................. PM2793

[51] Int. Cl.$^6$ .................................................. A61M 16/00
[52] U.S. Cl. ....................... 128/204.21; 128/204.18; 128/204.23
[58] Field of Search ............... 128/204.18, 204.21, 128/204.23, 716, 205.25, 204.26, 207.18

[56] References Cited

U.S. PATENT DOCUMENTS

| | | | |
|---|---|---|---|
| 3,834,383 | 9/1974 | Weigl et al. | 128/145.8 |
| 3,840,006 | 10/1974 | Buck et al. | 128/145.8 |
| 3,863,630 | 2/1975 | Cavallo | 128/145.6 |
| 3,961,627 | 6/1976 | Ernst et al. | 128/145.8 |
| 3,972,327 | 8/1976 | Ernst et al. | 128/145.8 |
| 4,239,039 | 12/1980 | Thompson | 128/205.24 |
| 4,347,468 | 8/1982 | Wilke | 318/331 |
| 4,430,995 | 2/1984 | Hilton | 128/204.21 |
| 4,537,190 | 8/1985 | Caillot et al. | 128/204.22 |
| 4,570,631 | 2/1986 | Durkan | 128/204.23 |
| 4,630,614 | 12/1986 | Atlas | 128/721 |
| 4,637,386 | 1/1987 | Baum | 128/204.21 |
| 4,686,974 | 8/1987 | Sato et al. | 128/204.23 |
| 4,782,832 | 11/1988 | Trimble et al. | 128/207.18 |
| 4,823,788 | 4/1989 | Smith et al. | 128/205.24 |

(List continued on next page.)

FOREIGN PATENT DOCUMENTS

| | | |
|---|---|---|
| 0 171 321 | 12/1986 | European Pat. Off. . |
| 0 505 232 A1 | 9/1992 | European Pat. Off. . |
| 238077 | 11/1969 | Russian Federation . |
| WO 82/03548 | 10/1982 | WIPO . |
| WO 86/05965 | 10/1986 | WIPO . |
| WO 87/02577 | 5/1987 | WIPO . |
| WO 88/10108 | 12/1988 | WIPO . |
| WO 92/11054 | 9/1992 | WIPO . |
| WO 93/21982 | 11/1993 | WIPO . |
| WO 94/23780 | 10/1994 | WIPO . |

OTHER PUBLICATIONS

Philipson, Eliot A., *Sleep Apnea—A Major Public Health Problem* (Editorials), The New England Journal of Medicine, Apr. 29, 1993; 328 (17), pp. 1271–1273.

Dement et al., *It's Time to Wake Up to the Importance of Sleep Disorders*, JAMA, Mar. 24/31, 1993–vol. 269, No. 12, pp. 1548–1549.

*Images of the Twenty–First Century*, Yongmin K., Seplman F. A.Seattle, Nov. 9–12, 1989, vol. II Part 1/06.

*A Microprocessor–Based Sleep Apnea Ventilator*, K. Behbehani et al., IEEE Engineering in Medicine & Biology Society 11th Annual International Conference, Ch. 2770, Jun. 1989, pp. 332–333.

Abstract—94308936.7.

*Primary Examiner*—Vincent Millin
*Assistant Examiner*—William J. Deane, Jr.
*Attorney, Agent, or Firm*—Holland & Hart LLP

[57] ABSTRACT

Apparatus and methods for the estimation of flow and the detection of breathing (respiration) in continuous positive airway pressure (CPAP) treatment are disclosed. CPAP apparatus typically includes a flow generator for supplying air to a mask via a gas delivery tube. With changing air flow, the flow generator's speed and/or driving electrical current will alter in a manner defined by the controlling circuitry. Signals can be derived from measurements of motor speed and current, and these signals vary cyclically with patient respiration. By filtering to reject non-respiratory components, the resultant signal can be utilised to determine the instants in time at which the patient starts to inhale and exhale. The filtered signal also can be linearised using a predetermined knowledge of the pressure/flow/speed characteristics of the flow generator, and thus to derive a volumetric measure of airflow.

12 Claims, 5 Drawing Sheets

U.S. PATENT DOCUMENTS

| | | | |
|---|---|---|---|
| 4,828,257 | 5/1989 | Hatch | 128/204.18 |
| 4,905,687 | 3/1990 | Ponkala | 128/204.21 |
| 4,915,103 | 4/1990 | Visveshwara et al. | 128/204.23 |
| 4,938,212 | 7/1990 | Snook et al. | 128/205.24 |
| 5,024,219 | 6/1991 | Dietz | 128/204.21 |
| 5,117,819 | 6/1992 | Servidio et al. | 128/204.18 |
| 5,239,995 | 8/1993 | Estes et al. | 128/204.21 |
| 5,245,995 | 9/1993 | Sullivan et al. | 128/104.23 |
| 5,385,142 | 1/1995 | Brady et al. | 128/204.22 |
| 5,443,061 | 8/1995 | Champain et al. | 128/204.21 |
| 5,490,502 | 2/1996 | Rapoport et al. | 128/204.21 |
| 5,535,738 | 7/1996 | Estes et al. | 128/204.21 |

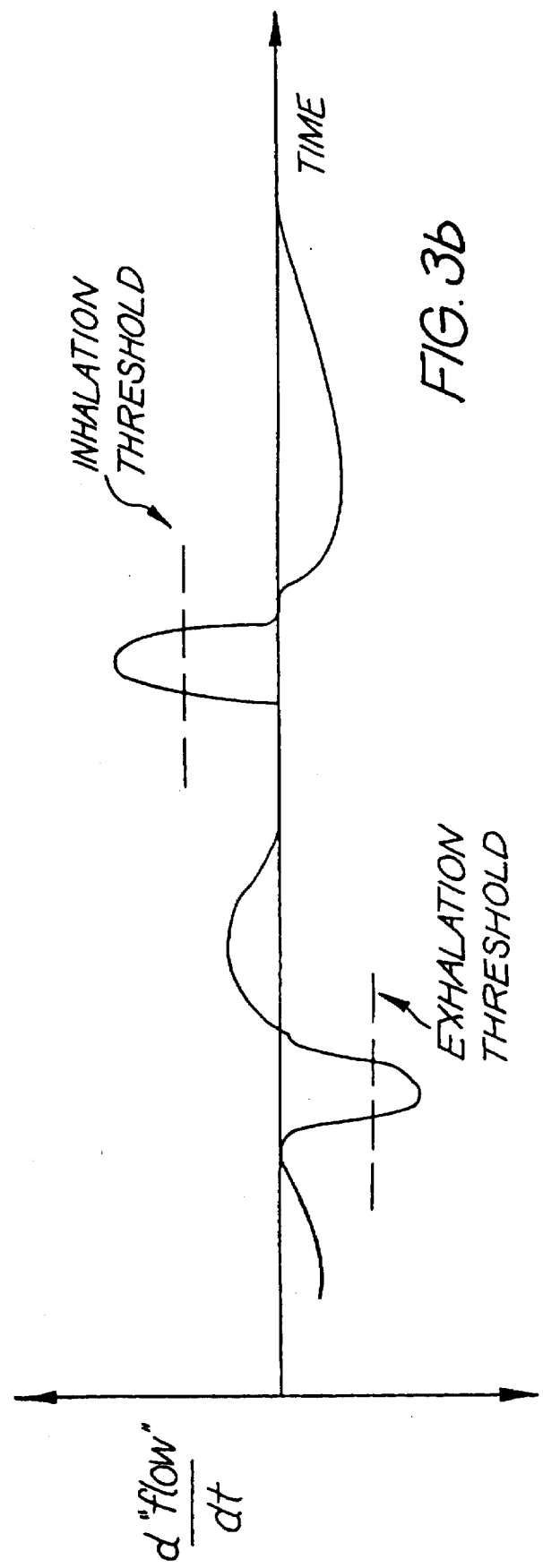

5,740,795

ESTIMATION OF FLOW AND DETECTION OF BREATHING IN CPAP TREATMENT

FIELD OF THE INVENTION

This invention relates to methods and apparatus for the estimation of flow and the detection of breathing (respiration) in continuous positive airway pressure (CPAP) treatment.

BACKGROUND OF THE INVENTION

The administration of CPAP is common in the treatment of Obstructive Sleep Apnea (OSA) syndrome and Upper Airway Resistance syndrome. The fundamental disclosure of CPAP is made in the specification of PCT AU82/00063, published under WO 82/03548. CPAP treatment effectively acts as a pneumatic splint of a patient's upper airway by the provision of a positive air pressure at approximately 10 cm $H_2O$, although pressures in the range of approximately 2–20 cm $H_2O$ are encountered. More sophisticated forms of CPAP, such as bi-level CPAP and autosetting CPAP, are described in U.S. Pat. No. 5,245,995. Common to all forms of CPAP is a nose, mouth or face mask fitted to a patient having connection via a flexible air delivery tube to an air flow generator.

In more advanced forms of CPAP treatment, the measurement of airflow in the air delivery tube is used to detect the average volume breathed by the patient and to determine whether that person is inhaling (inspiring) or exhaling (expiring). Currently this is done using an in-line sensor to measure flow directly, or by measuring the pressure drop across a restriction in the air delivery tube (or alternatively, the pressure drop along the air delivery tube). These methods require the use of additional transducers and, in some cases, additional wiring or tubing to connect the transducer to the appropriate point in the circuit.

In this specification any reference to a "mask" is to be understood as embracing a nose, mouth or combination nose and mouth (face) mask suitable for the administration of CPAP treatment. Furthermore, a "mask" can include nasal prongs (cannulae) that are inserted into the nares at the entrance to the airway.

SUMMARY OF THE INVENTION

It is a preferred object of the present invention to offer an improvement over existing methods at least by removing the need for additional transducers, wires or tubing to measure airflow. It is a further preferred object of the invention to detect respiration, and particularly inspiration and expiration.

Therefore the invention discloses a method for detecting respiration during the administration of continuous positive airway pressure (CPAP) treatment to a patient by CPAP apparatus, said CPAP apparatus including a flow generator for supplying air to a 'mask' via a gas delivery tube, said method comprising the steps of:

measuring a parameter indicative of power consumed by said flow generator to derive a power signal;

filtering said power signal to remove non-respiratory components; and sensing a change in said filtered signal as indicative of respiration.

The invention further discloses a method for detecting inspiration and expiration during the administration of CPAP treatment to a patient by CPAP apparatus, said CPAP apparatus including a flow generator supplying air to a 'mask' via a gas delivery tube, said method comprising the steps of:

measuring a parameter of said flow generator to derive an operating signal;

calculating from said operating signal a signal representative of flow due to respiration;

sensing a change in said flow signal;

comparing said change with a first threshold to detect start of inhalation if said first threshold is exceeded; and comparing said change with a second threshold to detect start of exhalation if said second threshold is exceeded.

The invention yet further discloses apparatus for the detection of respiration during the administration of CPAP treatment to a patient by CPAP apparatus, the CPAP apparatus including a flow generator for supplying air to a 'mask' via a gas delivery tube, said apparatus comprising:

means for measuring a parameter indicative of power consumed by said flow generator and deriving a power signal thereof;

means for filtering said power signal to remove non-respiratory components; and means for sensing a change in said filtered signal as being indicative of respiration.

The invention yet further discloses apparatus for detecting inspiration and expiration during the administration of CPAP treatment to a patient by CPAP apparatus, said CPAP apparatus including a flow generator supplying air to a 'mask' via a gas delivery tube, the apparatus comprising:

means for measuring a parameter of said flow generator to derive an operating signal;

means for calculating from said operating signal a signal representative of flow due to respiration;

means for sensing a change in said flow signal;

means for comparing said change with a first threshold to detect start of inhalation if said first threshold is exceeded; and means for comparing said change with a second threshold to detect start of exhalation if said second threshold is exceeded.

BRIEF DESCRIPTION OF THE DRAWINGS

Embodiments of the invention will now be described with reference to the accompanying drawings, in which:

FIGS. 3a and 3b are graphs of airflow, and the time derivative of airflow.

DETAILED DESCRIPTION OF PREFERRED EMBODIMENTS AND BEST MODE

A CPAP flow generator typically is realised by a small turbine powered by an electric motor. The speed of the motor is controlled by a feedback loop in that either the motor speed or the air pressure in the breathing circuit is measured and an error signal generated to increase or decrease drive to the motor or other regulating device, thus attempting to maintain either a constant motor speed or a constant CPAP treatment delivery pressure. Airflow in the breathing circuit is normally dictated by one or more of:

a) a constant, deliberate leak situated near the mask (or at the end of the nasal prongs) to ensure that patient rebreathing is minimal;

b) the patient's respiration; and c) any additional unintended leaks.

With changing airflow due to respiration, parameters such as the turbine motor's speed and/or current will alter in a manner defined by the motor or solenoid-operated spill valve control circuitry. The solenoid-operated spill valve has the function of maintaining constant delivery pressure.

Signals can be derived from the motor speed and power measurements, or from the spill valve position and power measurements. These measured signals vary cyclically with the patient's respiration. In general they also bear a non-linear relationship to the actual volumetric flow which can, if required, be linearised using previously determined pressure/flow/speed characteristics of the turbine system to give a volumetric measure of patient respiration (flow).

Without linearisation, the signal can be used to detect the points at which the patient starts to inhale and exhale. These points are crucial to the correct working of bi-level CPAP machines which present to the patient a smaller pressure at exhalation than inhalation, and in machines which seek to automatically vary the CPAP pressure in line with the patient's clinical needs. The cyclical variation of the respiratory component in the signal is extracted by identifying the more slowly changing non-respiratory component and subtracting this from the original signal. Alternatively, the minimum value of the cyclic component can be detected and stored and thereafter subtracted from the original signal.

Figure 1A:
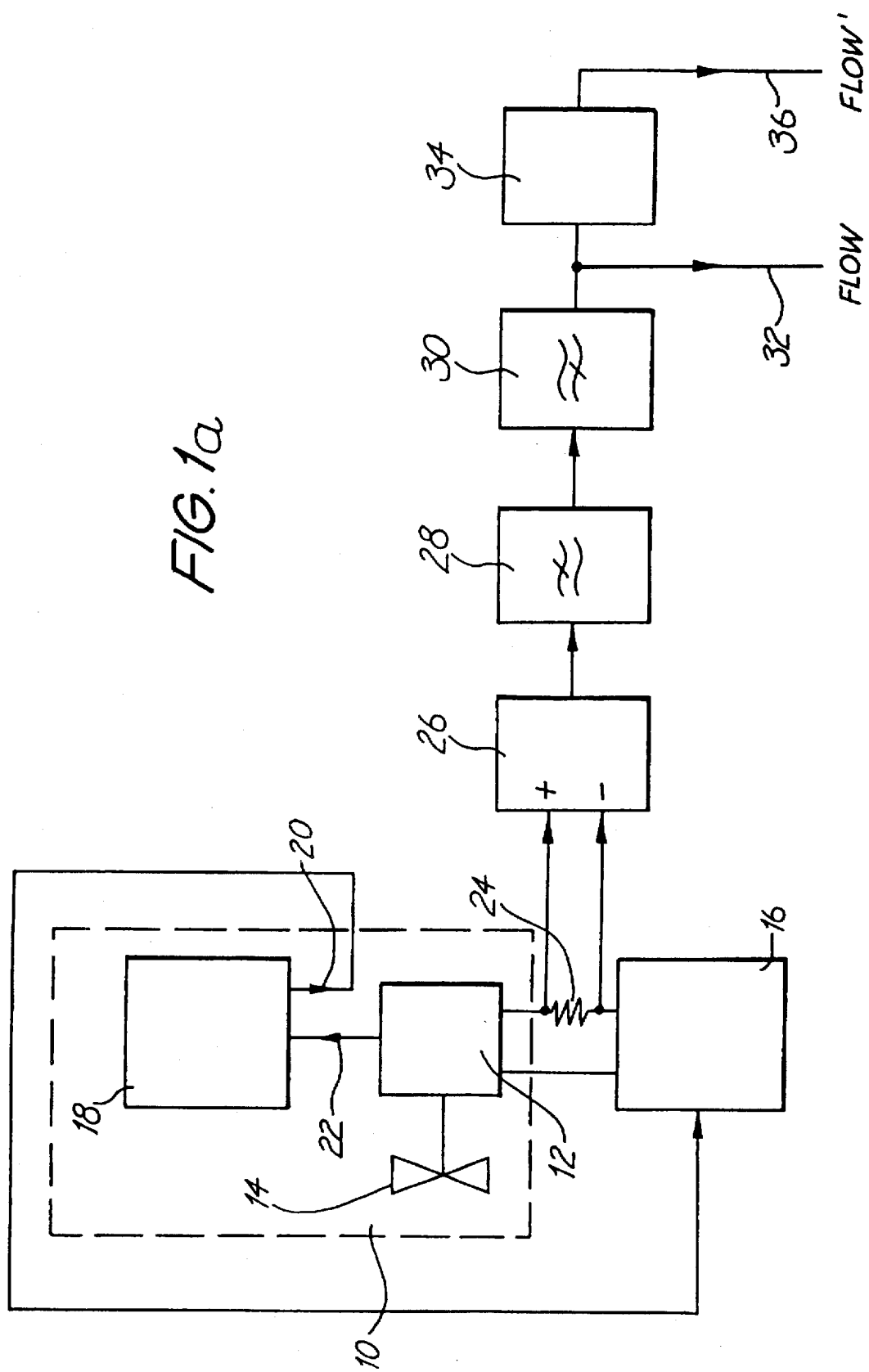
FIGS. 1a and 1b are schematic diagrams of two flow detection systems.
Figure 1B:
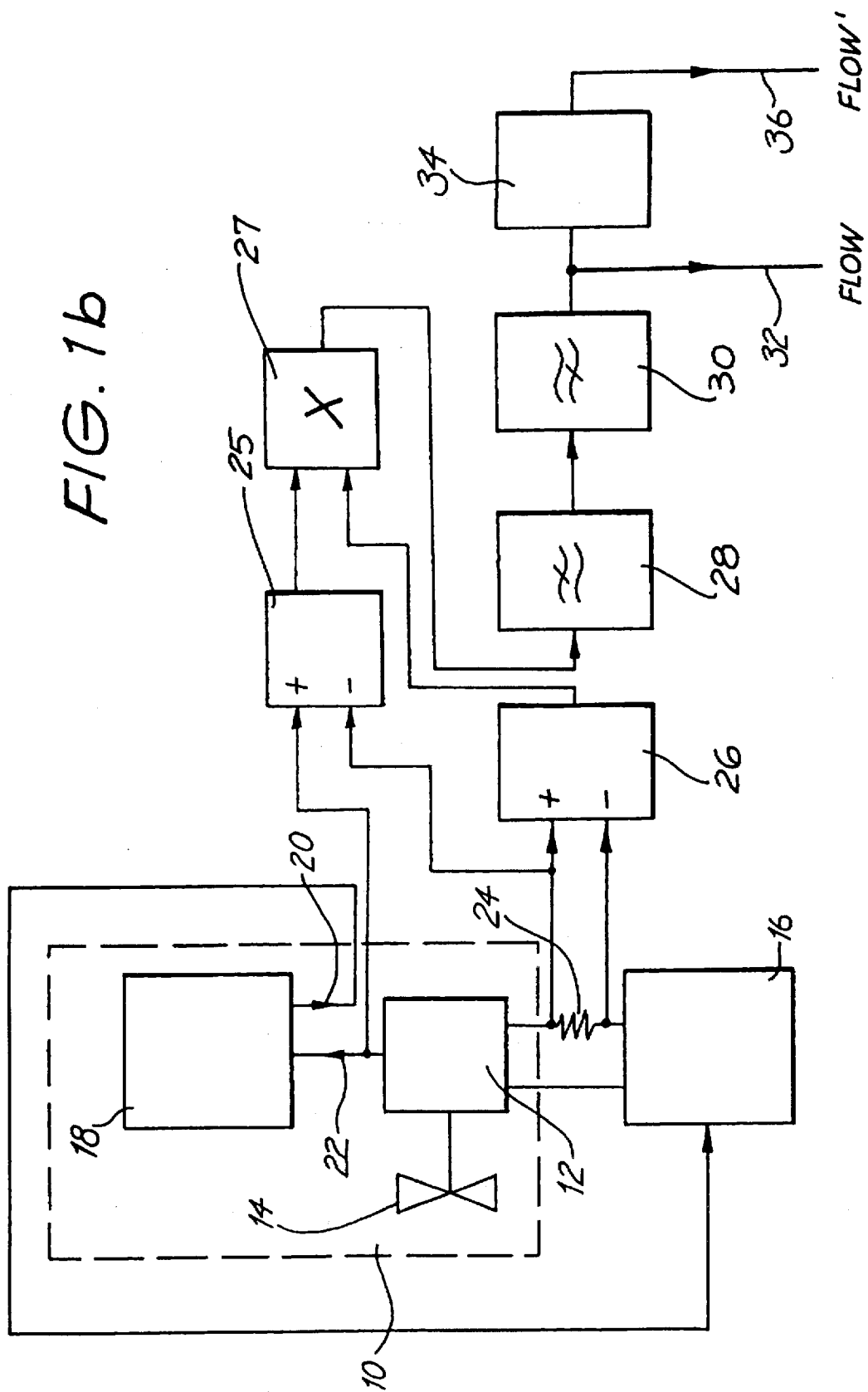

Embodiments implementing this methodology, are shown in the accompanying drawings. In FIGS. 1a and 1b, a flow generator 10 comprises an electric motor 12 that drives a turbine 14. The turbine 14 provides a supply of air for the administration of CPAP treatment, transported to the patient's mask by an air delivery tube (not shown). The motor 12 receives electrical power from a power supply 16. Also comprising a part of the flow generator 10 is a motor controller 18, which issues a control signal 20 to the power supply 16 to control the motor speed and thus the speed of the turbine 14 and, in turn, the flow rate in the air delivery tube. Furthermore, a speed feedback signal 22 is input to the motor controller 18 to provide a signal upon which speed regulation can be based.

As shown in FIG. 1a, one of the interconnecting wires between the power supply 16 and the motor 12 is provided with a current sensing resistor 24. This resistor therefore detects current demanded by the motor 12, represented as the voltage appearing across the resistor 24. That voltage is sensed and input to a differential amplifier 26, thus producing an output signal representative of motor current (and thus also motor power). This output signal is then provided to a low-pass filter circuit 28 having an upper limiting frequency of, say, 20 Hz. The low-pass filter circuit 28 removes high frequency electrical noise, and also tends to average the signal. The filtered signal is then passed through a high-pass filter 30, typically with 0.5 Hz cut-off, to remove the non-respiratory components.

FIG. 1b shows an alternative arrangement to that shown in FIG. 1a. Optionally, the voltage drop across the motor 12 also can be measured via a differential amplifier 55. The output voltage thereof is then multiplied with the motor current signal previously derived by the differential amplifier 26 by a multiplier 27 to produce a measure of the time instantaneous power consumed by the motor. This time instantaneous power signal then is provided to the low pass filter circuit 28, and processing proceeds as described above. In many implementations, current alone will be a sufficient indicator of motor power, however in other cases the real instantaneous power will advantageously be determined as shown in. FIG. 1b.

Figure 3A:
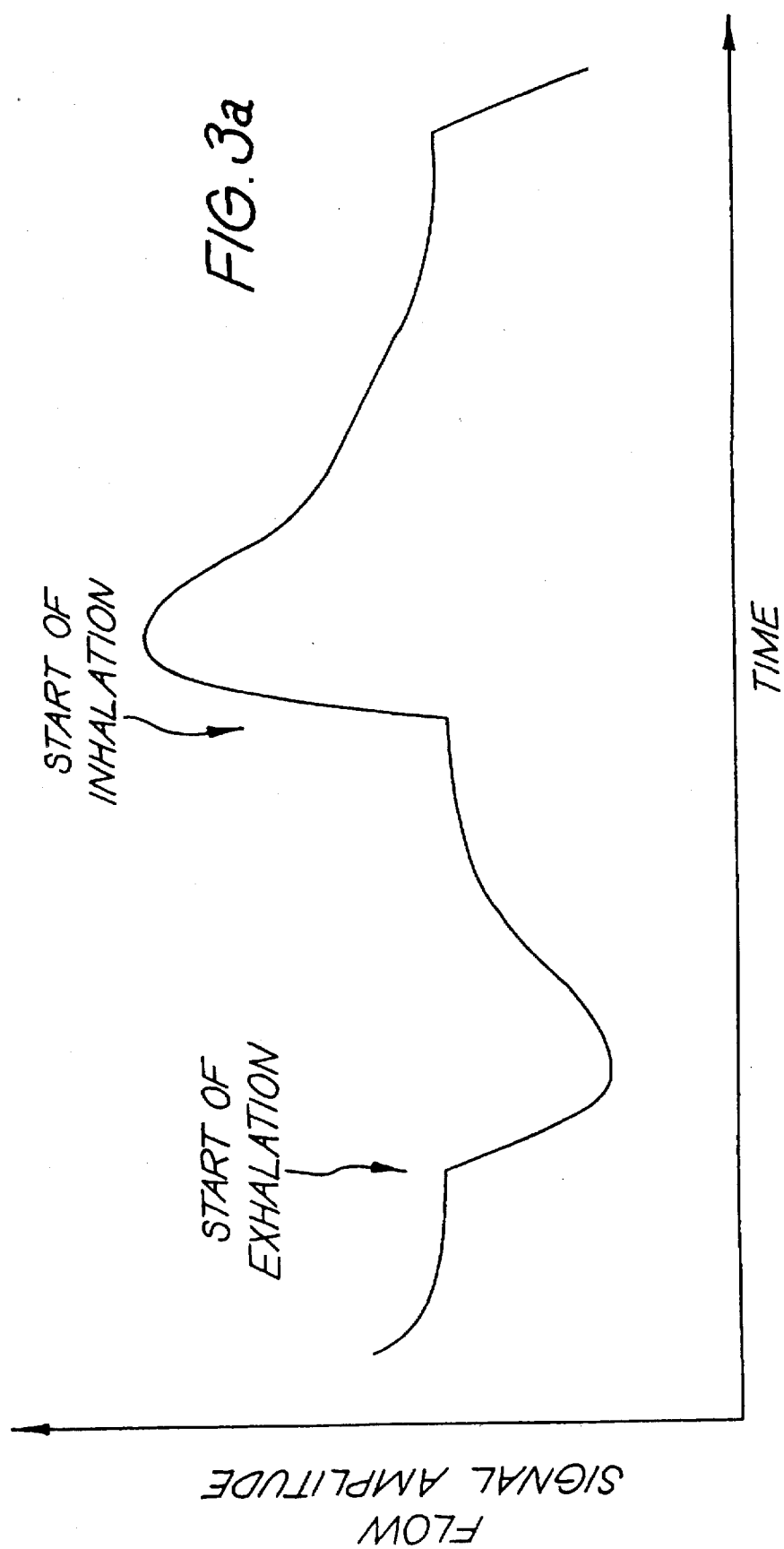

The output of the high-pass filter circuit 30, shown as output signal 32, is supplied to an inhalation/exhalation detector (not shown) which functions to determine the start of inhalation and exhalation by locating the sudden changes of signal amplitude and/or polarity following a segment having a low rate of change with time and being of a given minimum duration, typically 0.2 second. FIG. 3a shows a typical flow characteristic, and identifies both the start of inhalation and exhalation events, that are detected by the methodology described. Therefore, the output signal 32 (FLOW) provides an indication of the instances of inhalation and exhalation, and these points are critical to the correct working of bi-level CPAP machines, for example.

Alternatively, the output from the low-pass filter 28 can be input to a negative peak detector (not shown) which triggers a sample and hold circuit (also not shown) to latch the minimum point of the respiratory fluctuation. The detected minimum point of respiratory fluctuation can be updated periodically, typically as an exponentially past-time weighted sum of present and previous minimum measurements.

Figure 2:
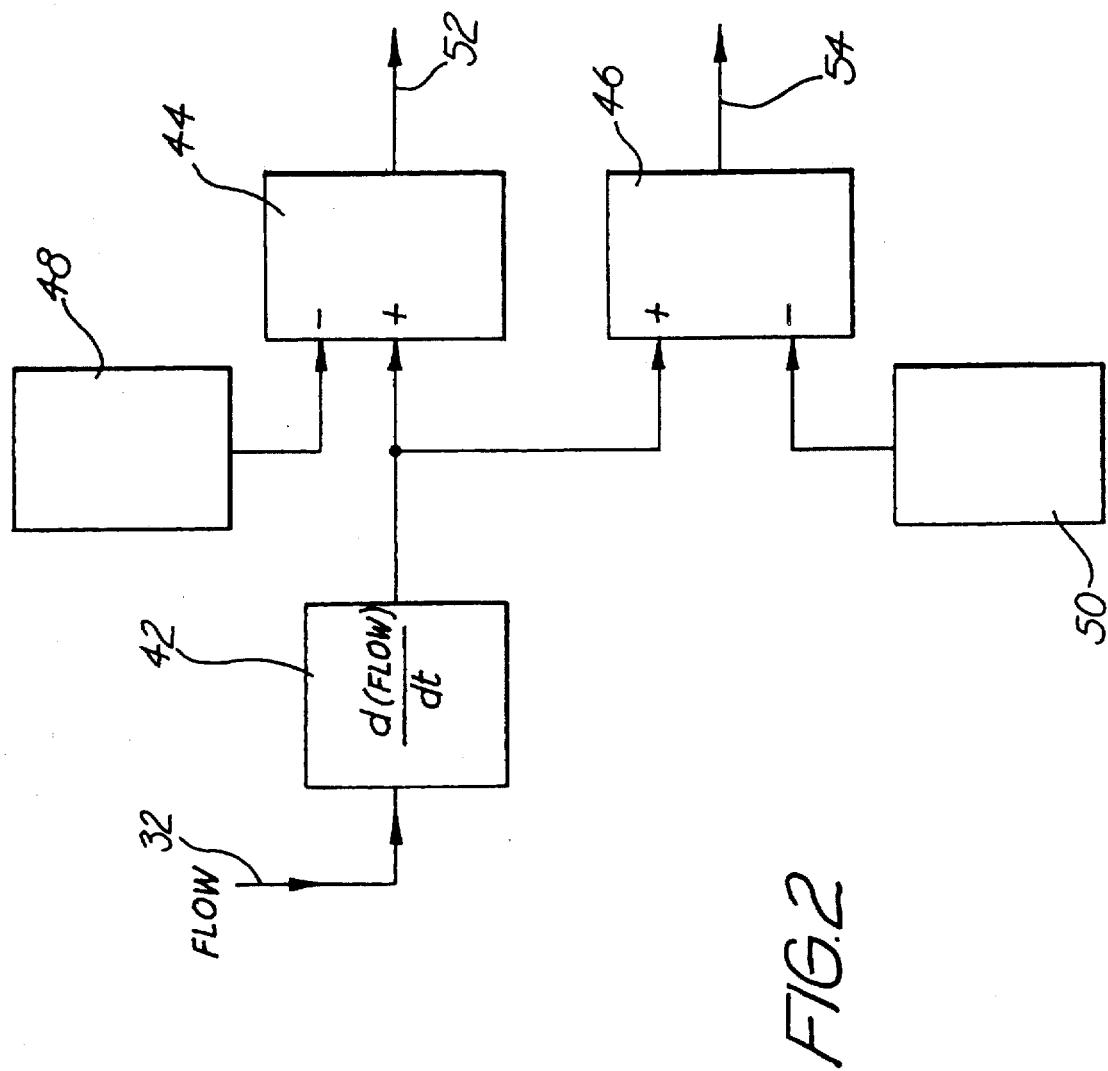
FIG. 2 is a schematic diagram of an inhalation/exhalation detector.

FIG. 2 shows another method and apparatus for the detection of inhalation and exhalation events. As shown, a band-limited differentiator 42 receives the FLOW signal 32, derived from the high-pass filter circuit 30. The output from the differentiator 42 is supplied to a pair of comparators 44,46. This output signal, as a time differential, is represented in FIG. 3b. Associated with each comparator 44,46 is a threshold generator 48,50. These generators 48,50 respectively have a threshold value for detecting inhalation and exhalation, as is shown in FIG. 3b. Therefore, the comparator 44 will compare the time differentiated flow signal output from the differentiator 42 with the threshold value supplied by the threshold generator 48, and when that value is exceeded (in the negative sense) an inhalation detection signal 52 is output. The other comparator 46 functions in a similar way to output an exhalation detection signal 54 in the event that the time differentiator flow signal exceeds (in a positive sense) the threshold value set by the threshold generator 50.

In another embodiment, the low-pass filtered, signal (the output of the low-pass filter 28) derived from the motor current can be digitised and input to a microcomputer where the subsequent signal processing described above is performed digitally. In this implementation threshold levels and decision times can be varied dynamically to track the changing shape of the patient's respiratory flow.

If the output signal 32 is linearised by a linearisation element 34 to produce a linearised flow signal 36 (FLOW'), then, as previously described, this gives a volumetric measure of patient respiration by comparison with a previously determined pressure/flow/speed characteristics of the turbine system.

Modifications and alterations, as would be apparent to one skilled in the art, can be made without departing from the basic inventive concepts. All such modifications and alterations are to be considered within the scope of the present invention, embodiments of which have been hereinbefore described.

What I claim is:

1. A method for detecting respiration during the administration of continuous positive airway pressure (CPAP) treatment by a CPAP system, said CPAP system including an electrical motor coupled to a turbine for supplying breathable gas to a mask via a gas delivery tube, said method comprising the steps of:

measuring motor voltage to derive a motor voltage signal;

measuring motor current to derive a motor current signal;

deriving an instantaneous motor power signal as a multiplication of said motor voltage signal and said motor current signal;

filtering said instantaneous motor power signal to remove non-respiratory components; and sensing a change in said filtered true motor power signal as being indicative of a change in respiratory phase.

2. The method as claimed in claim 1, whereby said sensing step comprises performing a time differentiation of said filtered instantaneous motor power signal.

3. The method as claimed in claim 2, comprising the further steps of:

comparing said differentiated instantaneous motor power signal with a first threshold value to detect start of inhalation phase if said first threshold value is exceeded; and comparing said differentiation true motor power signal with a second threshold value to detect start of exhalation phase if said second threshold value is exceeded.

4. The method as claimed in claim 3, comprising the further steps of:

linearising said filtered instantaneous motor power signal with respect to ones of predetermined characteristics of said gas delivery tube and said mask relating flow to consumed power to provide a volumetric measure of respiratory flow.

5. A method for detecting the start of inspiratory and expiratory phases of respiration during the administration of continuous positive airway pressure (CPAP) treatment by CPAP apparatus, said CPAP apparatus including an electrical motor coupled to a turbine for supplying breathable gas to a mask via a gas delivery tube, said method comprising the steps of:

measuring motor voltage to derive a motor voltage signal;

measuring motor current to derive a motor current signal;

driving an instantaneous motor power signal as a multiplication of said motor voltage signal and said motor current signal;

filtering said instantaneous motor power signal to remove non-respiratory components;

comparing said filtered signal with a first threshold value to detect start of inhalation phase if said first threshold value is exceeded; and comparing said filtered signal with a second threshold value to detect start of exhalation phase if said second threshold value is exceeded.

6. An apparatus for the detection of respiration during the administration of CPAP treatment by a CPAP system, said CPAP system including an electrical motor coupled to a turbine for supplying breathable gas to a mask via a gas delivery tube, said apparatus comprising:

means for measuring motor voltage to derive a motor voltage signal;

means for measuring motor current to derive a motor current signal;

means for deriving an instantaneous motor power signal as a multiplication of said motor voltage signal and said motor current signal;

means for filtering said true motor power signal to remove non-respiratory components; and means for sensing a change in said filtered true motor power signal as being indicative of a change in respiratory phase.

7. The apparatus as claimed in claim 6, wherein said means for sensing includes means for performing a time differentiation of said filtered instantaneous motor power signal.

8. The apparatus as claimed in claim 7, further comprising:

comparison means for comparing said differentiated instantaneous motor power signal with a first threshold value to detect start of inhalation phase if said first threshold value is exceeded, and for comparing said differentiated instantaneous motor power signal with a second threshold value to detect start of exhalation phase if said second threshold value is exceeded.

9. An apparatus for the detection of respiration during the administration of CPAP treatment by a CPAP system, the CPAP system including a flow generator for supplying breathable gas to a mask via a gas delivery tube, said apparatus comprising:

means for measuring motor voltage to derive a motor voltage signal;

means for measuring motor current to derive a motor current signal;

means for deriving an instantaneous motor power signal as a multiplication of said motor voltage signal and said motor current signal;

means for filtering said true motor power signal to remove non-respiratory components, said filtered signal being indicative of respiration; and means for comparing said filtered signal with a first threshold value to detect start of inhalation phase if said first threshold value is exceeded, and to compare said filtered signal with a second threshold value to detect start of exhalation phase if said second threshold value is exceeded.

10. A system for the administration of CPAP treatment, said system comprising:

an electrical motor;

a turbine coupled with said electrical motor for supplying breathable gas;

a gas delivery tube coupled with said turbine to receive said breathable gas;

a mask coupled with said delivery tube to deliver said breathable gas; and control means to control said motor and hence pressure of breathable gas delivered by said turbine, said control means including:

(a) means for measuring motor voltage to derive a motor voltage signal;

(b) means for measuring motor current to derive a motor current signal;

(c) means for deriving an instantaneous motor power signal as a multiplication of said motor voltage signal and said motor current signal;

(d) means for filtering said instantaneous motor power signal to remove non-respiratory components; and (e) means for sensing a change in said filtered instantaneous motor power signal as being indicative of a change in respiratory phase.

11. The system as claimed in claim 10, wherein said means for sensing includes:

means for performing a time differentiation of said filtered true motor power signal.

12. The system as claimed in claim 11, wherein said control means further comprises:

comparison means for comparing said differentiated true motor power signal with a first threshold value to detect start of inhalation phase if said first threshold value is exceeded, and for comparing said differentiated true motor power signal with a second threshold value to detect start of exhalation phase if said second threshold value is exceeded.

* * * * *